United States Patent
Jacob et al.

(10) Patent No.: US 9,902,072 B2
(45) Date of Patent: Feb. 27, 2018

(54) TELEPRESENCE SYSTEM

(75) Inventors: Dirk Jacob, Marktoberdorf (DE);
Marc-Walter Ueberle, Friedberg (DE);
Thomas Neff, München (DE); Martin Kuschel, München (DE); Tobias Ortmaier, Hemmingen (DE)

(73) Assignee: KUKA Roboter GmbH, Augsburg (DE)

(*) Notice: Subject to any disclaimer, the term of this patent is extended or adjusted under 35 U.S.C. 154(b) by 408 days.

(21) Appl. No.: 13/992,377

(22) PCT Filed: Dec. 1, 2011

(86) PCT No.: PCT/EP2011/071476
§ 371 (c)(1),
(2), (4) Date: Jul. 10, 2013

(87) PCT Pub. No.: WO2012/076390
PCT Pub. Date: Jun. 14, 2012

(65) Prior Publication Data
US 2013/0282179 A1    Oct. 24, 2013

(30) Foreign Application Priority Data
Dec. 8, 2010  (DE) .................. 10 2010 062 648

(51) Int. Cl.
*B25J 13/06*     (2006.01)
*B25J 9/16*      (2006.01)
(Continued)

(52) U.S. Cl.
CPC .............. *B25J 13/06* (2013.01); *A61B 34/30* (2016.02); *A61B 34/35* (2016.02); *B25J 9/1689* (2013.01);
(Continued)

(58) Field of Classification Search
None
See application file for complete search history.

(56) References Cited

U.S. PATENT DOCUMENTS

| | | | |
|---|---|---|---|
| 2007/0010256 A1 | 1/2007 | Klabunde et al. | |
| 2009/0034479 A1* | 2/2009 | Wakayama | H04L 45/16 370/332 |
| 2011/0306986 A1* | 12/2011 | Lee | B25J 9/1689 606/130 |

FOREIGN PATENT DOCUMENTS

| | | |
|---|---|---|
| DE | 10 2004 012 042 A1 | 9/2005 |
| WO | 2010/025943 A1 | 3/2010 |

OTHER PUBLICATIONS

European Patent Office; Search Report/Written Opinion in International Patent Application No. PCT/EP2011/071476 dated Mar. 9, 2012; 13 pages.

(Continued)

*Primary Examiner* — Firmin Backer
*Assistant Examiner* — Shawna M Kingston
(74) *Attorney, Agent, or Firm* — Wood Herron & Evans LLP

(57) ABSTRACT

A telepresence system includes a man-machine interface and a teleoperator configured to communicate bidirectionally with the man-machine interface via a communications channel. The teleoperator performs actions based on first signals generated due to a manual operation of the man-machine interface and transmitted over the communication channel, and sends second signals to the man-machine interface over a second communication channel. At least one buffer device buffers signals transferred through the communication channel and releases the signals delayed so that the signals coming from the man-machine interface and the signals (Continued)

coming from the teleoperator each are transmitted through the communication channel with an effective constant time delay.

11 Claims, 2 Drawing Sheets

(51) Int. Cl.
    *G06F 19/00*     (2018.01)
    *A61B 34/30*     (2016.01)
    *A61B 34/35*     (2016.01)
(52) U.S. Cl.
    CPC ...... *G06F 19/3418* (2013.01); *G06F 19/3481* (2013.01); *G05B 2219/40147* (2013.01); *G05B 2219/40195* (2013.01); *G05B 2219/45119* (2013.01)

(56) References Cited

OTHER PUBLICATIONS

Zlee et al.; Bilateral Teleoperation of Multiple Cooperative Robots Over Delayed Communication Networks: Application; published Apr. 2005; 6 pages.

\* cited by examiner

TELEPRESENCE SYSTEM

CROSS-REFERENCE

This application is a national phase application under 35 U.S.C. § 371 of International Patent Application No. PCT/EP2011/071476, filed Dec. 1, 2011 (pending), which claims the benefit of German Patent Application No. DE 10 2010 062 648.1 filed Dec. 8, 2010, the disclosures of which are incorporated by reference herein in their entirety.

TECHNICAL FIELD

The invention relates to a telepresence system.

BACKGROUND

In the telepresence or tele-operation system, robots are remotely controlled over relatively great distances. In this system, commands entered by an operator at an operator console or input device are sensorially detected, processed, and transmitted to a remotely located teleoperator. An application of such systems is the tele-manipulated surgery, in which for example a doctor manually moves several robotic arms through his input console, which move for example a medical instrument in order to treat a patient, in particular to operate on it. WO 2010/025 943 A1 discloses an example of such medical workplace.

SUMMARY

The technical task of the invention is to provide an improved telepresence system.

The technical task of the invention is resolved by a telepresence system comprising A man-machine interface, A teleoperator that is arranged to bidirectionally communicate through a communication channel with the human-machine interface, and which is designed to perform an action on the basis of first signals generated due to a manual operation of the man-machine interface and transmitted over the communication channel, based on the action performed to respond to its environment and, in response to the reaction to its environment, to send to the man-machine interface assigned second signals through the second communication channel, and at least one buffer device, which is adapted to buffer the signals transferred through the communication channel and to release them delayed so that the signals coming from the man-machine interface and the signals coming from the teleoperator each are transmitted through the communication channel with an effective constant time delay.

The telepresence system according to the invention is designed such that a person can control the teleoperator by means of the human-machine interface over the communication channel. The teleoperator is formed, for example, as at least one robot arm having a plurality of formed members connected by means of joints, drives for moving the members, and a fixing device and a control device for controlling the drives of at least one robot arm.

During the operation of the telepresence system according to the invention the teleoperator reacts with its environment in such a way that if it hits an object, a force acts on the teleoperator. This information is transmitted over the communication channel of the man-machine interface so that it can provide the person for example with haptic feedback.

In particular for reasons of stability, it may be desirable that the communication channel delays signals to the teleoperator with the same period as it delays signals to the man-machine interface. To ensure this, the telepresence system of the invention comprises at least one buffer device, which is adapted to buffer and generate in a delayed pattern the signals transferred through the communication channel so that the signals coming from the man-machine interface and the signals coming from the teleoperator are each transmitted through the communication channel with an effective constant time delay. Preferably, as is provided according to a variant of the telepresence system of the invention that the at least one buffer device is arranged to buffer and delay the signals transmitted through the communication channel so that the signals coming from the man-machine interface and the signals coming from the teleoperator are effectively transmitted through the communication channel with the same time delay.

This makes it possible, even with relatively large separate delays in the bidirectional communication channel, as is provided according to a preferred embodiment of the telepresence system of the invention, that its man-machine interface is designed such that it subjects the first signals, which are generated as the result of the manual operation of the man-machine interface, to a passivating transformation, especially a scattering transformation in order to get first transformed signals and to transmit them via the communication channel to the teleoperator, where the teleoperator is designed to send back the received first transformed signals to perform the action, to subject the second signals to a passivating transformation, in particular to a scattering transformation, to obtain second transformed signals and to transmit them via the communication channel to the man-machine interface, and the human-machine interface is designed to transform back the received second signals. The scattering transformation as such is known to a person skilled in the art, and it serves to passivate a communication channel, whereby the stability reserves of the telepresence system of the invention can be increased.

The at least one buffer device can for example be configured in such a manner that it buffers and delays the signals transmitted over the communication channel. The buffer can be for example integrated in the teleoperator or in the man-machine interface.

According to a variant of the telepresence system of the invention the at least one buffer device is configured such that it buffers delays the signals transmitted over the communication channel so that the signals coming from the man-machine interface and the signals coming from the teleoperator are transmitted through the communication channel with the same length of time that corresponds to a maximum time delay caused by the communication channel.

According to a preferred embodiment of the telepresence system of the invention, the buffer device is configured in such a manner as to buffer and delay the first transformed signals transmitted over the communication channel so that the teleoperator transforms back the time delayed first signals transformed by the buffer device. According to this variant, the invented telepresence system comprises a further buffer device for buffering and delaying the second transformed signals transmitted through the communication channel, so that the man-machine interface transforms back the signals delayed by the further buffer device. Thus it is possible, depending on in which direction the communication channel delays more the transmitted signals, to constantly buffer and delay signals so that the signals transmitted from the man-machine interface and the signals coming from the teleoperator are transmitted over the communication channel with the same delay.

The time delay PT1 of the buffer device and the time delay PT2 of the further buffer device may be determined as follow:

$$PT2 = Tmax - T1$$

$$PT1 = Tmax - T2,$$

where Tmax is at least the maximum time delay of the communication channel, and T1 is the time delay of the communication channel in the direction of man-machine interface to the teleoperator, and T2 is the time delay of the communication channel in the direction from the teleoperator to human-machine interface.

The telepresence system of the invention may be designed in such a manner as to automatically determine the time delay of the communication channel by means of time measurements on the man-machine interface and the teleoperator.

For a synchronization of the telepresence system of the invention it can be provided that it is designed to trigger the timing of the communication channel for the signals sent from the man-machine interface by means of the clock of the man-machine interface, to trigger the clock of the teleoperator by means of the clock of the communications channel for signals transmitted towards the teleoperator, and to trigger the timing of the communication channel towards the man-machine interface by means of the clock of the teleoperator. The telepresence system according to the invention may further be designed to compare the timing of the communication channel towards the man-machine interface of transmitted signals and the clock of the man-machine interface, and to detect a lack of synchronization of the telepresence system based on the comparison. Are for example these two bars out of sync or out of phase, it can be concluded that a lack of synchronization.

The telepresence system according to the invention is in particular designed as a medical workplace.

Depending on the configuration of the telepresence system according to the invention, which can also be referred to as a tele-operation system, a human operator is enabled to be active in a remote environment by means of the teloperators. In this case, the user commands the teleoperator via the man-machine interface, where the teleoperator is designed for example as a robot in the remote environment.

The telepresence system according to the invention is formed bidirectionally, i.e., signals are transmitted not only from the man-machine interface to the teleoperator, but also in the opposite direction. The teleoperator measures, for example, different environmental values and reflects them to the man-machine interface, which is in particular an environment remote to the operator. Commanded and reflected signals are exchanged by a communication channel, for example over the Internet.

The telepresence system according to the invention is in particular designed as a bilateral, kinesthetic-tactile telepresence system, in which in particular force and speed are exchanged.

In this case, for example an energy-prone loop between the operator and the teleoperator is closed. Delays in the communication channel can lead to instability of the whole system and are stabilized preferably by a passivating transformation, especially by means of the scattering transformation.

BRIEF DESCRIPTION OF THE DRAWINGS

An embodiment of the invention is depicted in the attached schematic drawings. In the drawings.

DETAILED DESCRIPTION

Figure 1:
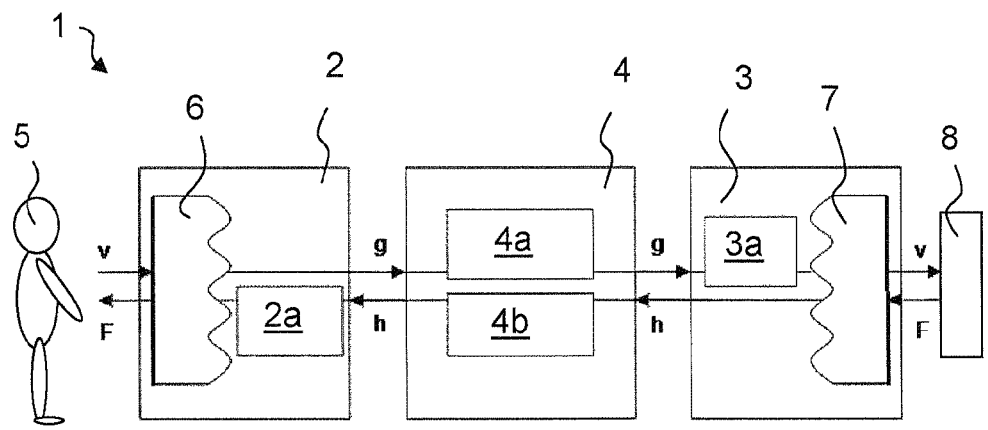
FIG. 1 shows a schematic diagram of a telepresence system.
Figure 2:
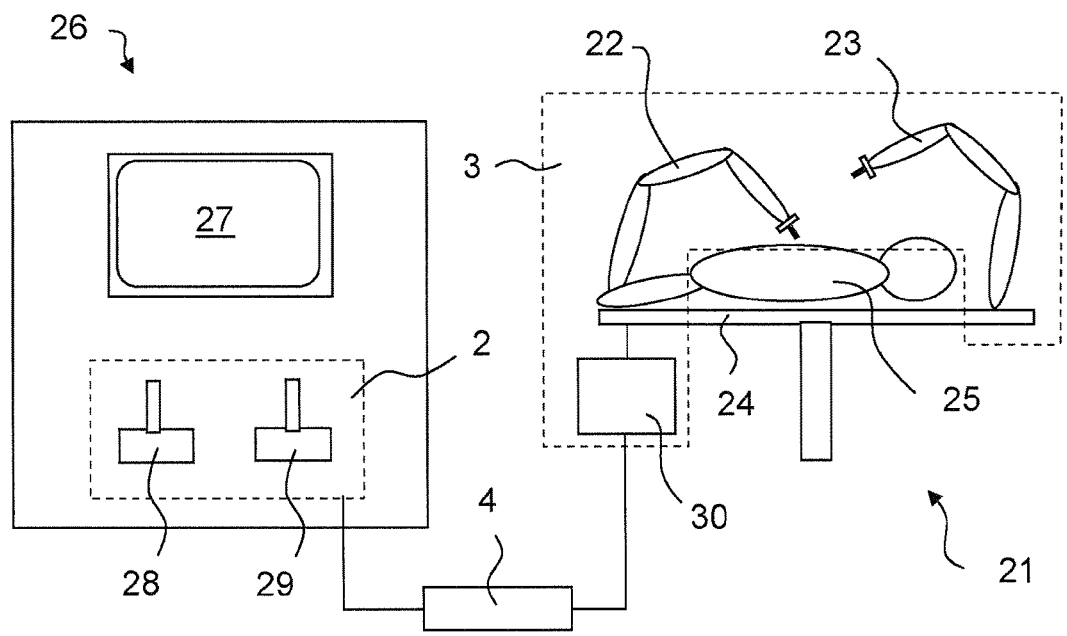
FIG. 2 shows an example of a medical workstation as a telepresence system.

FIG. 1 shows a schematic diagram of a telepresence system, which can be designed, for example, as a medical workplace shown in FIG. 2.

The telepresence system 1 has a man-machine interface 2 and a teleoperator 3, which communicate with each other via a communication channel 4. The communication channel 4 is for example a data transmission network, such as the Internet.

In the case of the present embodiment, the teleoperator 3 is implemented as a controller 30 and a plurality of robot arms 22, 23, each having a plurality of members connected by joints, their movement being controlled or regulated by the controller 30 that is connected to the communication channel 4. Using the robotic arms 22, 23, may for example a patient 25 lying on the operation table 24 be treated.

In the exemplary embodiment, the medical workstation 21 comprises a control panel 26 which, for example, a display device 27, and manual input devices 28, 29, by means of which a person, for example a surgeon, can tele-manipulate the robotic arms 22, 23. The two input devices 28, 29 are an example of the man-machine interface 2 of the telepresence system 1.

With a manual movement of the input devices 28, 29 by the person 5, for example, the input devices 28, 29 are moved with a speed v, so that the input devices 28, 29 or the man-machine interface 2 generates the appropriate signals, which have an information about the speed v.

In the case of the present embodiment, the man-machine interface 2 is configured such that it first subjects the velocity v to the so-called scattering transformation, which is well known to a person skilled in the art. This is illustrated by means of a function block 6 of the man-machine interface 2 in FIG. 1. As is well known to a person skilled in the art, the scattering parameters of the transformation are $$g = \frac{b \cdot v + F}{\sqrt{2 \cdot b}} \text{ and } h = \frac{b \cdot v - F}{\sqrt{2 \cdot b}}$$

with a freely selectable constant b.

The velocity transformed by the scattering transformation is then transmitted over the communication channel 4 to the controller 30, in general to the teleoperator 3. In the direction from the man-machine interface 2 to the teleoperator 3, the communication channel 4 represents a first sub-communication channel 4a with a time delay (communication latency) T1.

In the exemplary embodiment, the controller 30 or the teleoperator 3 is designed such that it first caches the transformed velocity received over the sub-communication channel 4a by means of a buffer 3a and it inversely transforms the transformed velocity delayed, so that, for example, the relevant robot arm 22, 23, being controlled by the control device 30, is moved according to the manual movement of the input devices 28, 29. The inverse transformation is illustrated by means of a function block 7 of the teleoperator 3 in FIG. 1. In the case of the present embodiment, the buffer 3a of the teleoperator 3 delays the signal assigned to the transformed velocity by a time period PT1.

In the exemplary embodiment, the teleoperator 3 interacts with the environment 8, which in comparison to the human-machine interface 2 is remote, such that the relevant robot arm 22, 23 introduces a medical instrument into the patient 25. Due to this interaction, the teleoperator obtains, for example, a force F, whose assigned signal is then subjected by the teleoperator 3 to a scattering transformation by means of the function block 7.

The force transformed by the scattering transformation is then transmitted through the communication channel 4 to the input devices 28, 29, in general to the man-machine interface 2.

In the direction from the teleoperator 3 to the man-machine interface 2, the communication channel 4 represents a second sub-communication channel 4b with a time delay (communication latency or communication delay) T2.

In the case of the present embodiment, the human-machine interface 2 is configured such that it initially caches the transformed force received through the communication channel 4b by means of a buffer 2a, and inversely transforms it delayed, so that the input devices 28, 29 send a feedback to the person 5 that is tactile to the relevant force on the robot arm 22, 23. The inverse transformation is illustrated in FIG. 1 by means of the function block 6 of the man-machine interface 2. In the case of the present embodiment, the buffer 2a of the man-machine interface 2 delays the force signal associated with the transformed force by a time period PT2.

To obtain a stable transmission of the signals over the communication channel 4, it is passivated using the scattering transformation. For this to be satisfactorily realized, the communication channel 4 should have in both directions a constant time delay of the transmitted signals. Preferably, both time delays can be the same, that is to say, the time delays of the sub-communication channels 4a, 4b may be the same and constant. In the case of real communication channels, this is generally not the case, because in reality they vary in general.

Since for the present embodiment both the signals from the man-machine interface 2 to the teleoperator 3 and the the signals from the teleoperator 3 to the human-machine interface 2 are subjected to the scattering transformation for transmission over the communication channel 4, in the case of the present embodiment there result the following parameters with the freely selectable constant b:

$$g_l = \frac{b \cdot v_{mmi} + F_{mmi}}{\sqrt{2 \cdot b}}$$

$$h_l = \frac{b \cdot v_{mmi} - F_{mmi}}{\sqrt{2 \cdot b}}$$

$$g_r = \frac{b \cdot v_{to} + F_{to}}{\sqrt{2 \cdot b}}$$

$$h_r = \frac{b \cdot v_{to} - F_{to}}{\sqrt{2 \cdot b}}$$

where:
$g_l$ is the outgoing scattering variable ("incident wave") on the side of the man-machine interface 2,
$g_r$ is the incoming scattering variable ("reflected wave") on the side of the teleoperator 3,
$h_r$ is the outgoing scattering variable on the side of the teleoperator 3, $g_r$ is the incoming variable scattering on the side of the man-machine interface 2,
$v_{mmi}$ is the velocity of the man-machine interface 2, and
$v_{to}$ is the velocity of the teleoperator 3, and
$F_{mmi}$ is the force that is imposed by the person on the man-machine interface 2, and
$F_{to}$ is the force exerted by the teleoperator 3 onto the remote environment 8.

At least in many, even if not in most or all cases, a maximum delay time Tmax of the communication channel 4 can be determined, which is not exceeded in particular with high probability.

In the case of the present embodiment, for this purpose there is provided bufferings of the received signals at the man-machine interface 2 and the teleoperator 3, for example, by the buffer 2a, 3a, which delay the commanded as well as the reflected signals so that a constant delay is achieved. By a time measurement at the human-machine interface 2 and at the teleoperator 3 and stamping of the communication packets transmitted over the communication channel 4, before the operation of the medical workplace 21, in general the telepresence system 1, the time periods T1, T2, i.e., the communication latency of the communication channel 4, are determine. The transmission duration of the commanded packages, that is to say the time period T1, which the data packet requires to arrive from the human-machine interface 2 to the teleoperator 3, when it is transmitted over the communication channel 4, can be expressed as follows:

$$T1 = t_2 - t_1$$

where $t_2$ is the point in time, at which the data packet reaches the teleoperator 3, and $t_1$ is the point in time, at which the data packet leaves the man-machine interface 2.

The transmission duration of the commanded packages, that is to say the time period T2, which the data packet requires to arrive from the teleoperator 3 to the human-machine interface 2, when it is transmitted over the communication channel 4, can be expressed as follows:

$$T2 = t_4 - t_1$$

where $t_3$ is the point in time, at which the data packet leaves the teleoperator 3, and $t_4$ is the point in time, at which the data packet reaches the man-machine interface 2.

Indicating the maximum delay time Tmax of the communication channel 4 and the time periods T1, T2, we can determine the lengths of the buffering (durations PT1, PT2) of the buffers 2a, 3a:

$$PT2 = T\max - PT1$$

$$PT1 = T\max - PT2$$

The result of synchronization and buffering is a constant communication latency of the communication channel 4 in both directions, which corresponds to the maximum delay time Tmax.

The maximum delay time Tmax is then used as a parameter of the scattering transformations.

Figure 3:
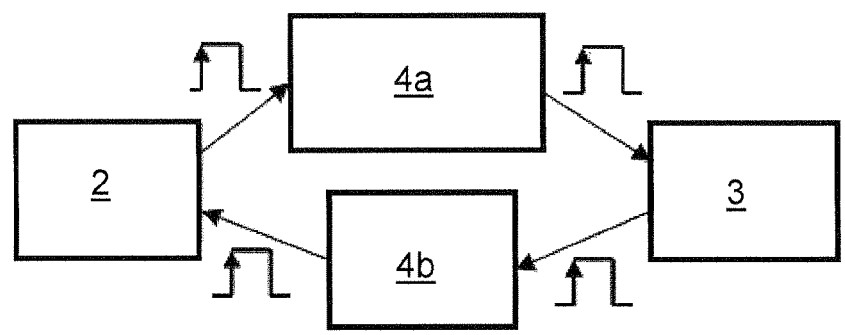
FIG. 3 is a block diagram illustrating synchronization and verification conducted for the telepresence system.

In the case of the present embodiment, the human-machine interface 2, the teleoperator 3 and the communication channel 4 are synchronized. FIG. 3 illustrates the synchronization of the man-machine interface 2, the communication channel 4 and the teleoperator 3.

First, the clock of the man-machine interface 2 is used as reference clock. This first triggers the clock of the sub-communication channel 4a of the communication channel 4 for the commanded signal, namely for the signal destined for the teleoperator 3. This then acts as a clock for the clock of the teleoperator 3. The clock of the teleoperator 3 triggers the clock of the sub-communication channel 4b of the communication channel 4 for the reflected signal, that is to say for the specific signal generated by the teleoperator 3 and destined for the man-machine interface 2.

The clock of the sub-communication channel 4b of the channel 4 is then compared with the reference clock, which is the clock of the man-machine interface 2. In case of a phase difference, an error in the synchronization of different clocks is detected.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

What is claimed is:

1. A telepresence system comprising:
   a man-machine interface,
   a teleoperator, which is designed to bi-directionally communicate over a communication channel with the man-machine interface, and which is designed to perform an action on the basis of first signals generated due to a manual operation of the man-machine interface and transmitted over the communication channel, based on the action performed to respond to its environment and, in response to the reaction to its environment, to send to the man-machine interface assigned second signals through the second communication channel, and
   at least one buffer device, which is adapted to buffer the signals transferred through the communication channel and to release them delayed so that the signals coming from the man-machine interface and the signals coming from the teleoperator each are transmitted through the communication channel with an effective constant time delay,
   wherein the signals coming from the man-machine interface are delayed by a first time which is determined by the difference in time between when a data packet reaches the teleoperator and when the data packet leaves the man-machine interface, and
   the signals coming from the teleoperator are delayed by a second time which is determined by the difference in time between when a data packet reaches the man-machine interface and when the data packet leaves the teleoperator.

2. The telepresence system of claim 1, whose at least one buffer device is so arranged as to buffer the signals transmitted through the communication channel and generate them with a delay so that the signals coming from the man-machine interface and the signals coming from the teleoperator are effectively transmitted over the communication channel with the same duration of time delay.

3. The telepresence system according to claim 1, whose human-machine interface is designed in such a manner that it subjects the first signals, which are generated as a result of the manual operation of the man-machine interface, to a passivating transformation, in particular to a scattering transformation in order to obtain first transformed signals and to send them through the communication channel to the teleoperator, wherein the teleoperator is designed to inversely transform the received first transformed signals in order to execute the action, to subject second signals to a passivating transformation, in particular a scattering transformation to obtain second transformed signals and to send them through the communication channel to the man-machine interface, and the man-machine interface is so designed as to inversely transform the received second signals.

4. The telepresence system according to claim 1, wherein the at least one buffer device buffers the signals transmitted through the communication channel and delays them.

5. The telepresence system according to claim 1, wherein the at least one buffer apparatus is so arranged as to buffer the signals transmitted through the communication channel and delays them in such a way that the signals coming from the man-machine interface and the signals coming from the teleoperator are transmitted through the communication channel with the same period of time corresponding to a maximum time delay related to the communication channel.

6. The telepresence system according to claim 3, wherein the buffer device buffers the signals transmitted through the communication channel and release them delayed so that the teleoperator inversely transforms the first signals transformed and delayed by the buffer device, and another buffer device is provided for buffering the second transformed signals transmitted through the communication channel and delays them so that the man-machine interface inversely transforms the second signals transformed and delayed by the buffer device.

7. The telepresence system according to claim 6, wherein the time delay PT1 of the buffer device and the time delay PT2 of the further buffer device may be determined as follows:

$$PT2 = T\max - T1$$

$$PT1 = T\max - T2,$$

where Tmax is at least the maximum time delay of the communication channel, and T1 is the time delay of the communication channel in the direction of man-machine interface to the teleoperator, and T2 is the time delay of the communication channel in the direction from the teleoperator to human-machine interface.

8. The telepresence system according to claim 7, which is so designed as to determine the time delay of the communication channel by measuring at the man-machine interface and the teleoperator.

9. The telepresence system according to claim 1, which is adapted to trigger the clock of the communication channel for the signals sent by the human-machine interface by means of the clock of the man-machine interface, to trigger the clock of the teleoperator by means of the clock of the communication channel for the signals transmitted in the direction of the teleoperator, to trigger the clock of the communication channel in the direction of the man-machine interface by the clock of the teleoperator, and by comparing the clock the communication channel of the signals transmitted in the direction of man-machine interface and the clock of the man-machine interface to detect a lack of synchronization of the telepresence system.

10. The telepresence system according to claim 1, wherein the teleoperator is formed as at least one robot arm with a plurality of members connected with hinges, drives for moving the members, and a fastening device, and a controller is designed for controlling the actuators of the at least one robot arms.

11. The telepresence system according to claim 1 that is formed as a medical workstation.

\* \* \* \* \*